Feb. 5, 1974 M. H. POIRIER Plant Pat. 3,470
IVY PLANT
Filed May 17, 1972
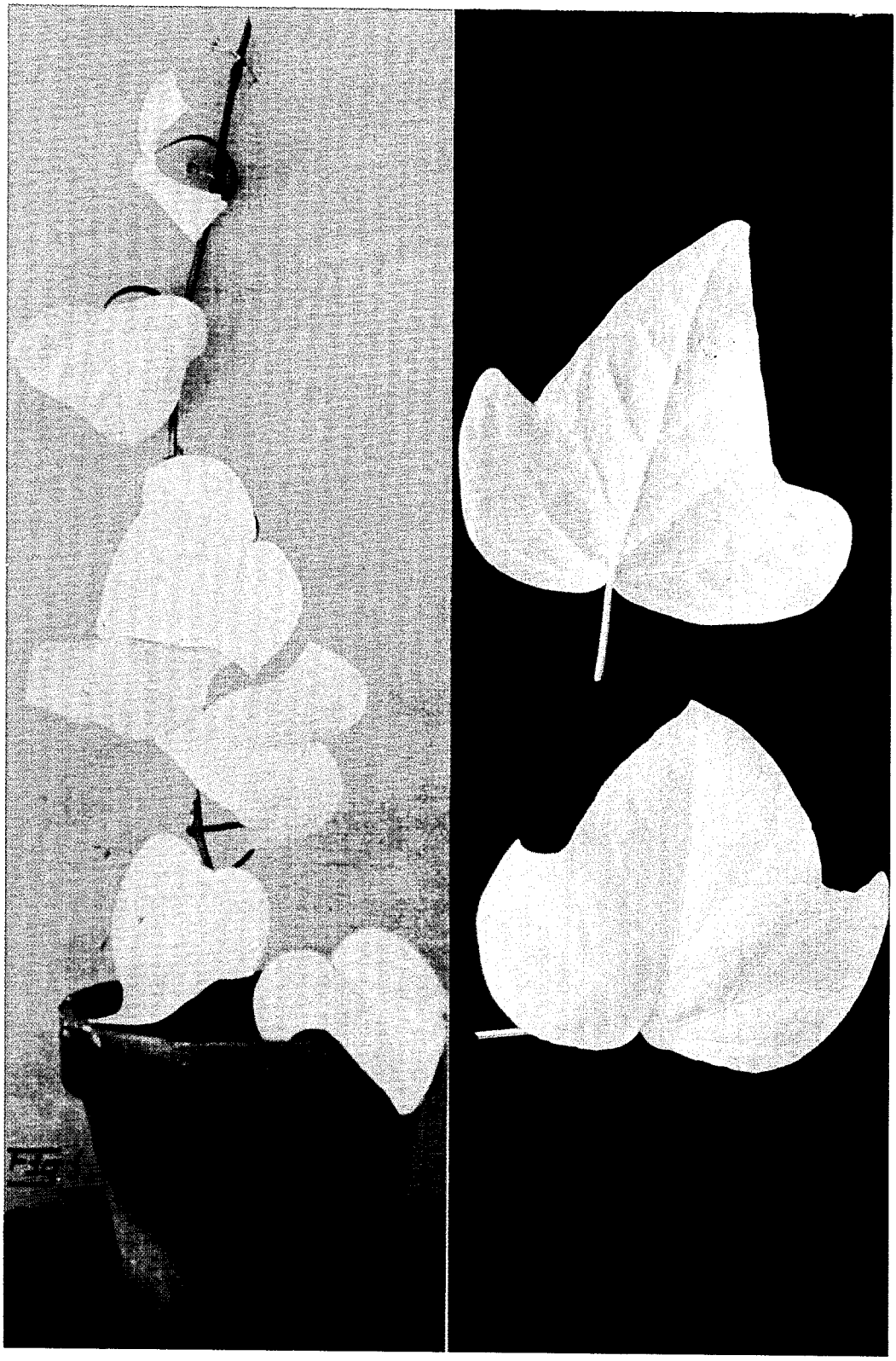

United States Patent Office

Plant Pat. 3,470
Patented Feb. 5, 1974

3,470

IVY PLANT

Mary Helen Poirier, 1701 Rosalind St.,
Sacramento, Calif. 95838

Filed May 17, 1972, Ser. No. 254,318
Int. Cl. A01h 5/00
U.S. Cl. Plt.—67 1 Claim

ABSTRACT OF THE DISCLOSURE

A mutation of *Hedera canariensis variegato* (Algerian variegated ivy) is distinctly characterized as a new variety by leaves which are all white (Plate 18–D–1 of Maerz and Paul Dictionary of Color). The new variety has been successfully asexually reproduced from cuttings as well as by ground-layering.

My discovery relates to a new variety of *Hedera canariensis variegato* which is useful in every way that other types of ivies are; namely, for climbing ground cover, ornamental potted plants, and the like.

This new variety is outstandingly different from the parent plant in respect to its leaf coloring. It is a sport of an unpatented variegated ivy, the mutation having been discovered by me in a collection of ivy plants I have grown for many years in my garden located in Sacramento, Calif. I constantly and diligently searched out the sports most nearly like my primary objective of a plant with all leaves entirely devoid of any kind of green coloring; and by reproducing these sports, and repeating the process again and again, I finally discovered the plant that I wanted, one in which all the leaves are all white. I have reproduced this new variety asexually, primarily by ground-layering and also by cuttings, and it has proven to reproduce true to type for a period of several years.

The accompanying photographic color print, designated as FIG. 1, illustrates a potted plant of my new discovery, showing the leaf coloration as closely as can be portrayed by photographic reproduction. The plant depicted is approximately four months old and in the figure it appears at about one-half true size. FIG. 1 also discloses the leaf configurations and arrangement on the stem.

FIG. 1 is a colored photographic reproduction, to an enlarged scale, of the upper side of a mature leaf of my new variety of ivy plant; and, FIG. 3 is a view similar to FIG. 2, but showing the under side of the same leaf.

The leaves are arranged quite far apart and in alternating sequence on opposite sides of the stems. There is relatively little branching in the younger plants, resulting in quick, vigorous growth. The young stems, including the nodes and petioles are reddish-purple in color. The vines produce aerial rootlets, which also assist in natural propagation.

The large leaves and profuse growing habit, which enables the plant to extend eight feet or more during a year, make it especially suitable as an outdoor climber or ground cover. However, when planted indoors, the leaves remain smaller and growth is slower, making a much more compact and very striking potted plant. Since the plant is not deciduous, it retains its beauty throughout the year. I have found that it grows best in shade or partial shade, and has proved over a number of years to be hardy in the Central Valley climate of California.

The outstanding feature of this new variety is the color of the leaves, which are white (yellowish-white) as illustrated in Plate 18–D–1 of the Maerz and Paul Dictionary of Color. The leaves are large, luxurious and glossy, with a texture resembling that of fine leather. They are three-lobed, with the central lobe larger in size and curving slightly downwardly in a uniform manner with the side lobes so as to present a leaf having a gracefully curved configuration.

The vein structure is also white, and is relatively prominent in size, although the veins are only slightly raised above the surface. The main veins run from the base of the leaf to the ends of each lobe in gently rolling furrows, so that the leaf takes on a very interesting contour as well as possessing an exciting color.

In size, the larger leaves of a mature plant range from three to over six inches wide and from three and one-half to seven inches long, growing on petioles from three to six inches long.

The petioles and attached leaves grow from every node, the nodes being from two to four inches apart along the stem.

The young stems, nodes and petioles are a reddish-purple, Plate 55–L–11 according to the Maerz and Paul Dictionary of Color. As the stems get older, they turn a greyish-brown and the texture becomes woody.

Another interesting feature of the new variety is the color taken on by the leaves in the winter when exposed to cold or frost. Around the extreme outer perimeter of the leaves, a band about 0.01 inch in width turns a reddish-purple color, similar to the color of the young stems, nodes and petioles; and dependent upon the extent of the cold or frost, the leaves themselves become partially or completely mottled with a lighter shade of this reddish-purple color, being identified as Plate 54–D–5 in Maerz and Paul Dictionary of Color. When warmer weather arrives in the spring, the reddish-purple coloration disappears and the leaves resume their customary white (yellowish-white) tone.

Having thus disclosed my discovery, I claim:

1. A new and distinct variety of ivy plant, as herein shown and described, characterized particularly by the white color of the large, luxuriously glossy leaves; by rapid and vigorous growth during summer; by the reddish-purple color of the nodes, petioles and young stems; and by the temporary mottling of this reddish-purple color into the leaves during frosty winter weather.

No references cited.

ROBERT E. BAGWILL, Primary Examiner